United States Patent
Sahlsten et al.

(10) Patent No.: US 12,327,528 B2
(45) Date of Patent: Jun. 10, 2025

(54) COMPENSATING FOR COLOUR VISION DEFICIENCY OF VIEWER

(71) Applicant: Varjo Technologies Oy, Helsinki (FI)

(72) Inventors: Oiva Arvo Oskari Sahlsten, Helsinki (FI); Mikko Strandborg, Helsinki (FI)

(73) Assignee: Varjo Technologies Oy, Helsinki (FI)

( * ) Notice: Subject to any disclaimer, the term of this patent is extended or adjusted under 35 U.S.C. 154(b) by 0 days.

(21) Appl. No.: 18/361,971

(22) Filed: Jul. 31, 2023

(65) Prior Publication Data

US 2025/0046261 A1 Feb. 6, 2025

(51) Int. Cl.
*G09G 3/36* (2006.01)
*G09G 3/34* (2006.01)
*A61B 3/06* (2006.01)

(52) U.S. Cl.
CPC ............ *G09G 3/3413* (2013.01); *G09G 3/36* (2013.01); *G09G 3/3607* (2013.01); *A61B 3/066* (2013.01); *G09G 2320/0233* (2013.01); *G09G 2320/0626* (2013.01); *G09G 2320/0666* (2013.01); *G09G 2330/021* (2013.01); *G09G 2354/00* (2013.01)

(58) Field of Classification Search
CPC .... A61B 3/066; G09G 3/3413; G09G 3/3607; G09G 3/3648; G09G 2320/0233; G09G 2320/0626; G09G 2320/0666; G09G 2330/021; G09G 2354/00
See application file for complete search history.

(56) References Cited

U.S. PATENT DOCUMENTS

| | | | | |
|---|---|---|---|---|
| 2008/0224986 A1* | 9/2008 | Huang | .................. | G09G 3/3413 345/102 |
| 2011/0148940 A1* | 6/2011 | Byun | .................... | G09G 3/3426 345/102 |
| 2012/0147163 A1* | 6/2012 | Kaminsky | .............. | G09G 5/028 345/590 |

FOREIGN PATENT DOCUMENTS

EP 2886039 A1 * 6/2015 ............. A61B 3/066

* cited by examiner

*Primary Examiner* — Julie Anne Watko
(74) *Attorney, Agent, or Firm* — Ziegler IP Law Group

(57) ABSTRACT

Disclosed is a backlight unit of a liquid crystal display device, the backlight unit having an array of light-emitting diodes (LEDs) of at least three different colours, wherein the LEDs are arranged as groups of LEDs within the array, each group including at least one LED of each of the at least three different colours; a control circuit that is to be employed to control individual LEDs in the array; and a controller configured to drive the control circuit to selectively decrease a brightness of LEDs of at least one of the at least three different colours in at least a part of the array.

13 Claims, 5 Drawing Sheets

COMPENSATING FOR COLOUR VISION DEFICIENCY OF VIEWER

TECHNICAL FIELD

The present disclosure relates to backlight units of liquid crystal display devices. Moreover, the present disclosure relates to display apparatuses including liquid crystal display devices having such backlight units. Furthermore, the present disclosure relates to methods for illuminating and displaying, such methods incorporating compensation for colour vision deficiency of viewer.

BACKGROUND

Colour vision deficiency, also commonly known as colour blindness, is a visual condition wherein a user's eyes are unable to distinguish between different colours when the user views any multi-colour visual content. The colour vision deficiency may occur due to any injury that may damage optic nerve or retina of the user's eyes, a genetic condition, a disease, medications, chemical exposure, aging, and similar. These occurrences may cause abnormalities in photoreceptors, i.e., cone cells in the retina of the user's eyes. The cone cells include a plurality of light-sensitive pigments that enable humans to recognize colours. There are three types of cone cells in the human eyes, i.e., short-wavelength cone cells (S-cones), medium-wavelength cone cells (M-cones), and long-wavelength cone cells (L-cones).

Referring to FIG. 1 (Prior Art), illustrated is a graphical representation 100 of a normalized spectral response of the cone cells for a standard eye vision of a human. Herein, a horizontal axis of the graphical representation 100 represents wavelength of light in nanometres, and a vertical axis of the graphical representation 100 represents the normalized spectral response of the cone cells (measured in units of linear energy). The plurality of light-sensitive pigments in the cone cells respond differently to light of different wavelengths. A normalized spectral response of the S-cones to light lying in a range of 400 nanometres to 550 nanometres is depicted by a curve 102 with a spectral peak at approximately 450 nanometres; a normalized spectral response of the M-cones to light lying in a range of 450 nanometres to 650 nanometres is depicted by a curve 104 with a spectral peak at approximately 540 nanometres; a normalized spectral response of the L-cones to light lying in a range 450 nanometres to 700 nanometres is depicted by a curve 106 with a spectral peak at approximately 580 nanometres. In other words, the S-cones are sensitive to the light of blue colour, the M-cones are sensitive to the light of green colour, and the L-cones are sensitive to the light of red colour. The colour vision deficiencies may be caused by overlapping of the spectral responses of the cone cells of different types. For example, in FIG. 1, it is noteworthy that even for the standard eye vision of humans, the normalized spectral response curves 104 and 106 of the M-cones and the L-cones overlap at least partially. Furthermore, for users suffering from red-green colour vision deficiency, the normalized spectral response curves 104 and 106 of the M-cones and the L-cones lie even closer to each other as compared to the normalized spectral response curves for the standard eye vision of the humans, thereby making it harder for such users to distinguish between the red colour and the green colour.

Conventionally, colourblind glasses are used to correct improper colour perception of the user's eyes. Different types of colourblind glasses are usable for different types of colour vision deficiencies. The colourblind sunglasses compensate for the overlapping of the spectral response curves of the cone cells of different types by blocking certain wavelengths of light so that the user's eyes can easily distinguish between different colours. However, colourblind sunglasses are cumbersome to use, may have different performance in different lighting conditions, and are effective only to a very limited extent. Moreover, the colourblind sunglasses provide an altered colour perception which often feels unnatural to users and adversely affects the users' overall visual experience. Customization of colourblind sunglasses according to the colour vision deficiencies of the user is expensive, and may not be an accessible solution for public at large. Furthermore, nowadays, techniques are being developed so that display equipment itself compensates for the colour vision deficiencies by adjusting colours and/or brightness of the display equipment. However, such techniques are not yet properly developed, and thus they still do not properly compensate for the colour vision deficiencies of the user's eyes.

Therefore, in light of the foregoing discussion, there exists a need to overcome the aforementioned drawbacks.

SUMMARY

The aim of the present disclosure is to provide a backlight unit of a liquid crystal display device, a display apparatus including a liquid crystal display device having a backlight unit, a method for illuminating and a method for displaying, such methods incorporating compensation for colour vision deficiency of a viewer to enable distinguishing between colours for which the viewer has colour vision deficiency. The aim of the present disclosure is achieved by backlight units of liquid crystal display devices, display apparatuses including liquid crystal display devices having backlight units, and methods for illuminating and displaying, such backlights and methods incorporating compensation for colour vision deficiency of a viewer as defined in the appended independent claims to which reference is made to. Advantageous features are set out in the appended dependent claims.

Throughout the description and claims of this specification, the words "comprise", "include", "have", and "contain" and variations of these words, for example "comprising" and "comprises", mean "including but not limited to", and do not exclude other components, items, integers or steps not explicitly disclosed also to be present. Moreover, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWINGS

FIGS. 4A and 4B illustrate exemplary arrays of light-emitting diodes (LEDs) of at least three different colours, in accordance with different embodiments of the present disclosure;

FIG. 4C illustrates an exemplary part of the array of FIG. 4A in in which a brightness of the LEDs of the at least one of the at least three different colours is to be selectively decreased, in accordance with an embodiment of the present disclosure;

DETAILED DESCRIPTION OF EMBODIMENTS

Figure 1:
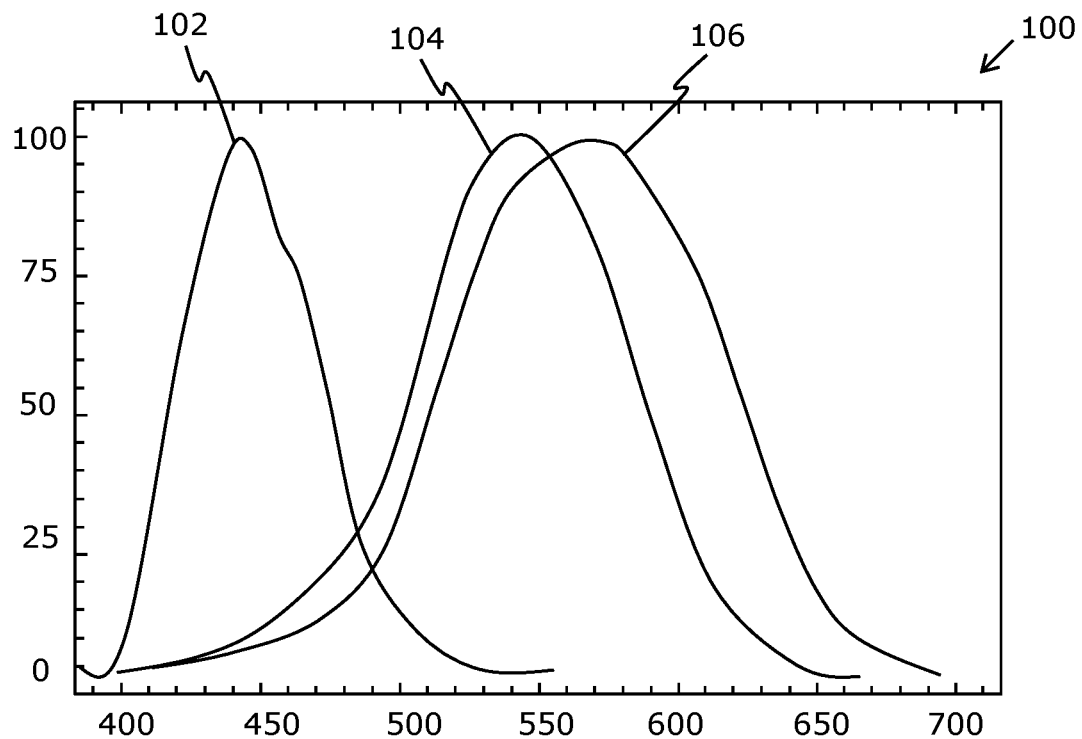
FIG. 1 (Prior Art), illustrates a graphical representation of a normalized spectral response of cone cells for a standard eye vision of a human

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In a first aspect, the present disclosure provides a backlight unit of a liquid crystal display device, the backlight unit comprising:
 an array of light-emitting diodes (LEDs) of at least three different colours, wherein the LEDs are arranged as groups of LEDs within said array, each group comprising at least one LED of each of the at least three different colours;
 a control circuit that is to be employed to control individual LEDs in said array; and
 a controller configured to drive the control circuit to selectively decrease a brightness of LEDs of at least one of the at least three different colours in at least a part of said array.

The aforementioned backlight unit comprises the controller which is configured to selectively control the brightness of the LEDs of the at least one of the at least three different colours to compensate for a colour vision deficiency specific to a user (namely, a viewer of the liquid crystal display device). Arranging the LEDs in the groups of LEDs in said array allows for controlling the brightness of the LEDs in each group in a selective manner, and yet produce light across the backlight in a uniform manner. This facilitates a comfortable viewing experience for the user. Such controlling is enabled synergistically by individually controlling each LED using the control circuit based on a spectral response of cone cells of the user's eyes. Herein, the control circuit is operatively synchronised with the controller in a manner that brightness of the LEDs of the at least one of the at least three different colours which may interfere with at least two other of the at least three different colours (i.e., colours that the user's eyes are not able to distinguish between due to his/her colour vision deficiency) is selectively decreased; this, in turn, makes the at least two other of the at least three different colours more prominent, thereby enabling the user's eyes to distinguish between the at least two other of the at least three different colours. In particular, selectively decreasing the brightness of LEDs of the at least one of the at least three different colours in at least the part of said array enables in improving colour perception and colour differentiability. Moreover, the backlight unit is easy to implement, simple, robust, fast, reliable, while having low power requirements.

In a second aspect, the present disclosure provides a display apparatus comprising:
 a liquid crystal display device having a backlight unit according to the first aspect; and
 a processor configured to:
  drive the backlight unit, according to a plurality of predefined options, to display images to a user via the liquid crystal display device, wherein a given predefined option corresponds to a predefined extent to which the brightness of the LEDs of the at least one of the at least three different colours is to be selectively decreased;
  receive a user input indicative of the user's selection of one of the plurality of predefined options; and
  drive the backlight unit according to the one of the plurality of predefined options selected by the user.

In the aforementioned display apparatus, the processor is configured to drive the backlight to selectively control the brightness of the LEDs based on one of the plurality of predefined options selected by the user. Such selective and user-specific controlling is enabled synergistically based on the user input, which triggers the control circuit to selectively decrease the brightness of the LEDs in the at least one of the at least three different colours. Hence, the user is provided with an option and a flexibility of selecting any of the plurality of predefined options, based on an extent and a specific type of colour vision deficiency that the user is suffering from. Furthermore, providing the plurality of predefined options enables the user to adjust the brightness of the LEDs to personalize their viewing experience, whilst also taking his/her colour vision deficiency into account. The display apparatus enables the user to selectively decrease the brightness of the LEDs as per her/his requirement, by voluntarily (and/or involuntarily) selecting one of the plurality of the predefined options. The backlight unit can easily by implemented in various types of display apparatuses, such as smart glasses, a head-mounted display, a television set, a display screen, or similar.

In a third aspect, the present disclosure provides a method for illuminating, the method being implemented by a backlight unit of a liquid crystal display device, wherein the backlight unit comprises an array of light-emitting diodes (LEDs) of at least three different colours, wherein the LEDs are arranged as groups of LEDs within said array, each group comprising at least one LED of each of the at least three different colours, and a control circuit, the method comprising:
 controlling, via the control circuit, individual LEDs in said array; and driving the control circuit for selectively decreasing a brightness of LEDs of at least one of the at least three different colours in at least a part of said array.

In the aforementioned method for illuminating, the brightness of the LEDs of the at least one of the at least three different colours is selectively controlled to compensate for a colour vision deficiency specific to a user. Arranging the LEDs in the groups of LEDs in said array allows for controlling the brightness of the LEDs in each group in a selective manner, and yet produce light across the backlight in a uniform manner. This facilitates a comfortable viewing experience for the user. Such selective controlling is enabled synergistically by individually controlling each LED based on a spectral response of cone cells of the user's eyes. As a result of selectively decreasing the brightness of the LEDs of the at least one of the at least three different colours, at least two other of the at least three different colours (between which the user's eyes are not able to distinguish) become more prominent, thereby enabling the user's eyes to distinguish between the at least two other of the at least three different colours. Moreover, the method described herein is simple, robust, fast, reliable, and easy to implement.

In a fourth aspect, the present disclosure provides a method for displaying, the method being implemented by a display apparatus comprising a liquid crystal display device having a backlight unit according to the first aspect, the method comprising:
   driving the backlight unit, according to a plurality of predefined options, to display images to a user via the liquid crystal display device, wherein a given predefined option corresponds to a predefined extent to which the brightness of the LEDs of the at least one of the at least three different colours is to be selectively decreased;
   receiving a user input indicative of the user's selection of one of the plurality of predefined options; and
   driving the backlight unit according to the one of the plurality of predefined options selected by the user.

In the aforementioned method for displaying, the brightness of the LEDS is selectively controlled based on one of the plurality of predefined options selected by the user. Such selective and user-specific controlling is enabled synergistically based on the user input, thereby triggering the control circuit to selectively decrease the brightness of the LEDs in the at least one of the at least three different colours. Hence, the user is provided with an option and a flexibility of selecting any of the plurality of predefined options, based on an extent and a specific type of colour vision deficiency that the user are suffering from. Furthermore, providing the plurality of predefined options enables the user to adjust the brightness of the LEDs to personalize their viewing experience, whilst also taking his/her colour vision deficiency into account. The aforementioned method enables the user to selectively decrease the brightness of the LEDs as per her/his requirement, by voluntarily (and/or involuntarily) selecting one of the plurality of the predefined options. The method described herein is simple, robust, fast, reliable, and easy to implement.

Optionally, the liquid crystal display device comprises the backlight unit (as described below), at least one polarizer, a first substrate and a second substrate, a liquid crystal material encased between the first substrate and the second substrate, a first electrode deposited on the first substrate and disposed between the liquid crystal material and the first substrate, a second electrode deposited on the second substrate and disposed between the liquid crystal material and the second substrate, and a colour filter. For the sake of convenience, all of the aforementioned components of the liquid crystal display device, except the backlight unit, can be collectively referred to as a liquid crystal display unit.

Herein, the term "polarizer" refers to an optical filter that allows light of a particular polarization orientation to pass through while blocking light of other polarization orientations. Optionally, the at least one polarizer comprises a first polarizer and a second polarizer. The first polarizer and the second polarizer work in conjunction with each other. Optionally, the first polarizer is any one of: a horizontal polarizer, a vertical polarizer, and wherein the second polarizer is another one of: the horizontal polarizer, the vertical polarizer. The horizontal polarizer allows light of a horizontal polarization orientation to pass therethrough, whereas the vertical polarizer allows light of a vertical polarization orientation to pass therethrough. In an example, the first polarizer may be the horizontal polarizer, and the second polarizer may be the vertical polarizer. Optionally, the first polarizer and the second polarizer are arranged on different sides of the liquid crystal display device. Alternatively, optionally, the first polarizer and the second polarizer are arranged on a same side of the liquid crystal display device.

Optionally, the first substrate and the second substrate are arranged parallel to each other. Optionally, the first substrate and/or the second substrate are optically transparent to enable passage of the light therethrough. The first substrate and/or the second substrate can be made of any one of: a glass, a polycarbonate, a plastic, a high-index plastic. Other examples of materials suitable for making the first substrate and/or the second substrate are well within the scope of the present disclosure.

The first electrode is made of a first electrode material, and the second electrode is made of a second electrode material. The first electrode material may be same as or different from the second electrode material. Herein, a given electrode material (namely, the first electrode material and/or the second electrode material) is optically transparent, thereby enabling a given electrode (namely, the first electrode and/or the second electrode) to be optically transparent. The optical transparency of the given electrode material enables passage of light therethrough. Examples of the given electrode material may include, but are not limited to, indium tin oxide (ITO), doped zinc oxide (ZnO; ZnO being doped with aluminium or hydrogen), a conductive polymer, and graphene. As an example, the first electrode could be a pixel electrode for enabling control of each LED (i.e., each pixel) individually, while the second electrode could be a common electrode that is connected to an electrical ground.

Optionally, the colour filter is arranged in front of the LEDs. Optionally, each LED of the array is aligned with a corresponding portion of the colour filter. A given portion of the colour filter allows passage of light of a corresponding wavelength range, whilst restricting passage of light of remaining wavelength ranges. Furthermore, a combination of the array of LEDs of the at least three different colours and the colour filter enables the liquid crystal display device to produce a broad spectrum of colours.

Throughout the present disclosure, the term "backlight unit" refers to a unit that is arranged behind the liquid crystal material of the liquid crystal display device when viewed from a perspective of a user, and which emanates light that, after passing through the liquid crystal material, enables production of images by the liquid crystal display device. The backlight unit is arranged with respect to the liquid crystal display device such that the light emanating from the backlight unit can pass through an entirety of the liquid crystal material. In some embodiments, the array of LEDs is arranged directly behind the liquid crystal material of the liquid crystal display device. Such a liquid crystal display device is a bottom-lit liquid crystal display device (namely, a direct-lit liquid crystal display device). In other embodiments, the array of LEDs is arranged around a perimeter edge behind the liquid crystal display. In such embodiments, the backlight unit optionally further comprises light guides to distribute the light emanating from the array of LEDs across the liquid crystal material. Such a liquid crystal display device is an edge-lit liquid crystal display device.

It will be appreciated that the light which emanates from the backlight unit, in use, comprises a broad spectrum of wavelengths due to the usage of the array of LEDs of the at least three different colours. Herein, the light of different colours (or, light of different spectral wavelengths) is emanated by adjusting the brightness of the LEDs of the at least three different colours, as each LED in the array of LEDs has a corresponding spectral emission characteristic. Hence, the backlight unit has adjustable spectral emission characteristics.

Optionally, each LED corresponds to a sub-pixel of the liquid crystal display device, and each group of LEDs within the array of LEDs correspond to a pixel of the liquid crystal display device. Hence, each pixel comprises at least three sub-pixels having respective ones of the at least three different colours. The groups of LEDs can be arranged within said array in a form of a matrix with varying dimensions, as will be described later.

Optionally, the backlight unit may further comprise an optical element such as a diffuser (for example, a diffusion sheet) that diffuses light emitted by the LEDs of the array. The diffuser is arranged in front of the backlight unit to scatter the light emitted by the backlight unit in different directions, and distribute the light evenly across the entire liquid crystal display device. A technical effect of diffusing light in such a manner is that it enables elimination of hotspots or localized bright spots, thereby providing uniform and consistent illumination.

In a first embodiment, the at least three different colours comprise a red colour, a blue colour, a green colour, and a white colour. A technical effect of the array of LEDs comprising the at least three different colours is that the broad spectrum of colours can be produced by controlling the brightness of LEDs of the red colour, the blue colour, the green colour, and the white colour, as the backlight unit works on a principle of additive colour. The array of LEDs of the at least three different colours are arranged in such a manner that during normal operation, when all the LEDs of the array are switched on, an overall white colour is produced uniformly across the liquid crystal display device. Herein, when switched on, the brightness of the LEDs can be controllable up to a predefined limit, wherein the predefined limit can be set by a normal colour calibration procedure. It will be appreciated that use of the LEDs of the white colour in the array facilitates in enhancing an overall brightness of the light emanating from the backlight unit.

Optionally, LEDs of the blue colour have a spectral peak that lies in a range of 425 nanometres to 460 nanometres, LEDs of the green colour have a spectral peak that lies in a range of 500 nanometres to 550 nanometres, LEDs of the red colour have a spectral peak that lies in a range of 600 nanometres to 700 nanometres.

In an example, the array of LEDs may comprise 64 LEDs that may be arranged in a form of a two-dimensional matrix of 8×8 LEDs. The LEDs of the array may be arranged as groups of LEDs within the array. Herein, these groups could comprise groups of LEDs arranged in a 2×2 matrix, groups of LEDs arranged in a 1×4 matrix, groups of LEDs arranged in a 4×1 matrix, groups of LEDs arranged in a 4×4 matrix, or similar. One such exemplary array of LEDs is illustrated in conjunction with FIG. 4A.

In a second embodiment, the at least three different colours comprise the red colour, the blue colour, the green colour, and a yellow colour. This combination of colours also works on the principle of additive colour. A technical benefit of this combination of colours is that it produces a wider colour gamut. It will be appreciated that use of the LEDs of the yellow colour in the array makes yellows more vibrant, and an entire image (when displayed on the liquid crystal display device) appears richer because human eyes are more sensitive to green and yellow than other colours.

In a third embodiment, the at least three different colours comprise a red colour, a blue colour, and a green colour, wherein for two or more of the at least three different colours, LEDs of a given colour are divided into at least two sets of LEDs having different spectral peaks, respectively. Throughout the present disclosure, the phrase "LEDs of a given colour" refers to LEDs that are to be employed to emit light of the given colour. The "spectral peak" of an LED refers to a particular wavelength (or a particular wavelength range) at which the LED emits light of the given colour most intensely (with respect to other wavelengths or other wavelength ranges). A technical effect of dividing the LEDs of the given colour into the at least two sets of LEDs having different spectral peaks is that a broad range of wavelengths are covered for the given colour (namely, the same colour), which enables in enhancing the perception of the given colour for users with colour vision deficiencies. Beneficially, this also provides a vibrant and a lifelike visual experience for the user.

Optionally, LEDs of the blue colour are divided into a first set of LEDs of the blue colour having a spectral peak that lies in a range of 410 nanometres to 430 nanometres, and a second set of LEDs of the blue colour having a spectral peak that lies in a range of 440 nanometres to 460 nanometres. Optionally, LEDs of the green colour are divided into a third set of LEDs of the green colour having a spectral peak that lies in a range of 490 nanometres to 530 nanometres, and a fourth set of LEDs of the green colour having a spectral peak that lies in a range of 560 nanometres to 590 nanometres. Optionally, LEDs of the red colour are divided into a fifth set of LEDs of the red colour having a spectral peak that lies in a range of 640 nanometres to 660 nanometres, and a sixth set of LEDs of the red colour having a spectral peak that lies in a range of 690 nanometres to 710 nanometres.

In an example, the array of LEDs may comprise 72 LEDs that may be arranged in a two-dimensional matrix of 8×9 LEDs. For the LEDs of the given colour having the different spectral peaks, some of the groups of LEDs within the array comprise LEDs of the given colour having a given spectral peak (from amongst the different spectral peaks), while a remainder of the groups of LEDs comprise LEDs of the given colour having another spectral peak (from amongst the different spectral peaks). These groups may comprise groups of LEDs arranged in a 2×1 matrix, groups of LEDs arranged in a 1×3 matrix, groups of LEDs arranged in a 2×3 matrix, groups of LEDs arranged in a 3×3 matrix, or similar. One such exemplary array of LEDs is illustrated in conjunction with FIG. 4B.

It will be appreciated that the term "at least three different colours" encompass various possible cases, for example, including a combination of the red colour, the blue colour, the green colour, and the white colour; a combination of red colour, the blue colour, and the green colour, wherein at least some LEDs of the red colour, the blue colour, and the green colour have different spectral peaks (namely, peak wavelengths); a combination of the red colour, the blue colour, the green colour, the yellow colour; and similar.

Furthermore, throughout the present disclosure, the term "control circuit" refers to a drive circuit that in operation controls the individual LEDs in the array to produce light of their corresponding colours. The control circuit allows for independent control and operation of the individual LEDS in the array. Such independent control and operation are employed to implement compensation of a colour vision deficiency of the user. Herein, the term "colour vision deficiency" refers to a visual condition wherein user's eyes are unable to perceive certain colours and/or are unable to distinguish between certain different colours. Examples of the colour vision deficiency may include, but are not limited to, red-green colour vision deficiency, blue-green colour vision deficiency, blue-yellow colour vision deficiency, and violet-red colour vision deficiency. Optionally, the control circuit comprise sub-circuits which are coupled with their corresponding LEDs in the array, to implement such individual controlling.

It will be appreciated that the controller is coupled to the control circuit, and is configured to send drive signals to the control circuit in order to selectively control the brightness of the LEDs in at least the part of said array. Herein, the part of said array could be any one of: a gaze-contingent part of said array, an entirety of said array. The controller could be implemented as any one of: a microcontroller, a processor, a microprocessor. The controller is configured to control the control circuit using at least one drive signal, wherein the at least one drive signal is used to drive the control circuit in a selective manner. Optionally, the at least one drive signal is at least one of: a voltage signal, a current signal.

Optionally, the controller is further configured to:
receive, from a gaze-tracking means, information indicative of a gaze direction of a user; and
select, based on the gaze direction of the user, the part of said array in which the brightness of the LEDs of the at least one of the at least three different colours is to be selectively decreased.

Herein, the term "gaze-tracking means" refers to a specialized equipment for detecting and/or following a gaze of the user, when the liquid crystal display device is used by the user. The gaze-tracking means (of the liquid crystal display device) is optionally communicably coupled to the controller. The term "gaze direction" refers to a direction in which the user is gazing. The gaze direction may be indicated by a gaze vector. The gaze-tracking means could be implemented as contact lenses with sensors, cameras monitoring a position, a size and/or a shape of a pupil of the user's eyes, and the like. Such gaze-tracking means are well-known in the art. The gaze-tracking means is configured to collect gaze-tracking data, which constitutes the information indicative of the gaze direction of the user. Then, the gaze-tracking means sends the gaze-tracking data (i.e., said information) to the controller. It will be appreciated that the information indicative of the gaze direction of the user is received (by the controller) repeatedly from the gaze-tracking means, as gaze of the user keeps on changing.

When the part of said array in which the brightness of the LEDs of the at least one of the at least three different colours is to be selectively decreased is selected based on the gaze direction of the user, said part is the gaze-contingent part of said array. A technical effect of selectively controlling the LEDs in the gaze-contingent part of said array, instead of the entirety of said array, is that the control circuit needs to control the LEDs individually according to the drive signal only in the gaze-contingent part, whilst controlling the LEDs in a remaining part of the array according to, for example, a generic drive signal. However, the drive signal is generated in a manner that the overall brightness in the gaze-contingent part is similar to the overall brightness in the remaining part.

Optionally, at least one of: a position, a shape, a size, of the part of the array of LEDs depends on an accuracy of the gaze-tracking means. It will be appreciated that when the user's gaze is directed (namely, focused) towards a point or a region within said array, a gaze direction of a first eye and a gaze direction of a second eye of the user are different from each other, and both the gaze directions converge at said point or said region. Since the gaze direction of the user is known, the gaze-contingent part of said array could be easily and accurately determined. Thereafter, based on the extent and the type of the colour vision deficiency from which the user is suffering, the at least one of the at least three different colours colour is selected from amongst the at least three different colours, and the brightness of the LEDs of the at least one of the at least three different colours is selectively decreased. In an example, when the gaze direction of the user lies towards a top-left portion of the liquid crystal display device in which the backlight unit is used, a top left corner part of the array is selected as the part of the array in which the brightness of LEDs of the at least one of the at least three different colours is selectively decreased.

Moreover, optionally, the at least one of the at least three different colours whose LEDs' brightness is selectively decreased comprises at least one of: a blue colour, a white colour, a red colour. The at least one of the at least three different colours whose LEDs' brightness is selectively decreased, is determined based on the type of the colour vision deficiency suffered by the user. A technical effect of this is that constituent colours pertaining to the type of the colour vision deficiency become distinguishable for the user when at least one of the other colours are suppressed. In this regard, in order to compensate for the colour vision deficiency of the user, light is emitted from the backlight unit in such a manner that there is a flat spectral emission across a range of visible light wavelength, except for a gap between colours which the user's eyes cannot distinguish (i.e., the constituent colours of the colour vision deficiency). Herein, when in use, the brightness of LEDs of the at least one of: the blue colour, the white colour, the red colour, may cause interference and/or blending, with at least two other of the at least three different colours. Hence, the brightness of the LEDs of the at least one of: the blue colour, the white colour, the red colour are selectively decreased so that the user's eyes are able to properly perceive the different colours, especially those colours for which the user has the colour vision deficiency.

In an example implementation, the user may suffer from red-green colour vision deficiency, wherein spectral peaks of respective cone cells of the user's eyes for the red colour and the green colour overlap to an extent that is more than an overlap for a standard eye vision of a human. Hence, in order to compensate for the excessive overlap, light may be emitted from the backlight unit such that a sharp gap is formed between said spectral peaks. This would mean that light of the green colour is to be moved to shorter wavelengths whereas light of the red colour is to be moved to longer wavelengths, so that they are easier to distinguish for the user having the red-green colour vision deficiency. Then, in order to maintain an overall colour balance, the brightness of LEDs of the white colour and/or the brightness of the LEDs of the blue colour may be selectively decreased.

In another example implementation, the user may suffer from blue-green colour vision deficiency, wherein the spectral peaks of respective cone cells of the user's eyes for the blue colour and the green colour overlap to an extent that is more than an overlap for a standard eye vision of a human. Hence, in order to compensate for the excessive overlap, light may be emitted from the backlight unit such that a sharp gap is formed between said spectral peaks. This would mean that light of the blue colour is moved to shorter wavelength whereas light of the green colour is to be moved to medium wavelengths, so that they are easier to distinguish for the user having the blue-green colour vision deficiency. Then, in order to maintain an overall colour balance, the brightness of the white colour and/or the brightness of the LEDs of the red colour may be selectively decreased.

In yet another example implementation, the user may suffer from blue-yellow colour vision deficiency, wherein the spectral peaks of respective cone cells of the user's eyes for a pair of the blue colour and the green colour, and for another pair of the green colour and the red colour, overlap to an extent that is more than an overlap for a standard eye vision of a human. Hence, in order to compensate for the excessive overlap, light may be emitted from the backlight unit such that a sharp gap is formed between said pairs of spectral peaks. This would mean that light of the blue colour is moved to shorter wavelengths whereas the light of the green colour and the red colour are moved to medium wavelengths and longer wavelengths, respectively, so that they are easier to distinguish for the user having the blue-yellow colour vision deficiency. Then, in order to maintain an overall colour balance, the brightness of LEDs of the white colour may be selectively decreased. Alternatively or additionally, in such a case, the brightness of LEDs of the red colour may be selectively decreased.

There will now also be considered a yet another example implementation where, for the two or more of the at least three different colours, LEDs of a given colour are divided into at least two sets of LEDs having different spectral peaks. In such an implementation for the blue-yellow colour deficiency, the brightness of the LEDs of the blue colour with a shorter wavelength out of the at least two sets of LEDs of the blue colour having different spectral peaks and the brightness of the LEDs of the green colour with a longer wavelength out of the at least two sets of LEDs of the green colour having different spectral peaks may be increased.

It will be appreciated that brightness of the LEDs of the green colour is not selectively decreased in any of the aforesaid example implementations as the green colour is commonly deficient in the aforementioned colour vision deficiencies and in other colour vision deficiencies well-known in the art. However, based on the colour vision deficiency of the user, the green colour can also be selectively decreased in some implementations. Optionally, in such a case, the at least one of the at least three different colours whose brightness is selectively decreased comprises the green colour.

Moreover, optionally, the at least one of the at least three different colours whose LEDs' brightness is selectively decreased comprises a white colour, wherein when selectively decreasing the brightness, the controller is configured to drive the control circuit to selectively switch off the LEDs of the at least one of the at least three different colours in at least the part of said array.

Such selective switching off of the LEDs of the at least one of the at least three different colours in at least the part of said array means that almost no light is emitted from the LEDs of the white colour from at least the part of said array. A technical effect of selectively switching off the LEDs of the at least one of the at least three different colours, wherein the at least one of the at least three different colours is the white colour, is that a compensatory effect for the colour vision deficiency of the user is maximized (albeit, at a cost of reduction of a total brightness of the liquid crystal display device). This is so because an interference of the light of white colour with other colours is nullified, thereby making the at least two other of the at least three different colours easily distinguishable and prominent.

As an example, the user may suffer from red-green colour deficiency. Hence, the brightness of the LEDs of the white colour may be selectively decreased by driving the control circuit to selectively switch off the LEDS of the white colour in at least the part of the array.

Moreover, optionally, the controller is further configured to drive the control circuit to selectively increase a brightness of LEDs of the at least two other of the at least three different colours in at least the part of said array. Notably, the at least two other of the at least three different colours in at least the part of said array comprise the constituent colours of the colour vision deficiency of the user. A technical effect of selectively increasing the brightness of the LEDs of the at least two other of the at least three different colours is that two or more colours between which the user's eyes cannot distinguish properly are made prominent and hence, are easily distinguishable. As a result of selectively increasing the brightness of the LEDs of the at least two other of the at least three different colours, a combined spectral emission has an attenuation at wavelength ranges around a particular wavelength. For example, when the user suffers from red-green colour vision deficiency, the brightness of the LEDs of the red colour and the green colour may be selectively increased. Hence, the combined spectral emission may attenuate at wavelength ranges around 600 nanometres.

Optionally, the at least two other of the at least three different colours whose LEDs' brightness is selectively increased comprises any one of: (i) a red colour and a green colour, (ii) a blue colour and a green colour. Such colour combinations correspond to typical combinations of constituent colours of common colour vision deficiencies in humans. A particular one of these colour combinations is selected depending on the type of the colour vision deficiency of the user. A technical effect of selectively increasing the LEDs' brightness of the at least two other of the at least three different colours according to any one of the aforementioned colour combinations is that the colour vision deficiency from which the user is suffering is properly compensated for, so that the user can easily distinguish between the at least two other of the at least three colours.

In an example implementation, the brightness of light emitted by respective LEDs of the green colour and the red colour is selectively increased when the user suffers from red-green colour vision deficiency. In another example implementation, the brightness of light emitted by respective LEDs of the blue colour and the green colour is selectively increased when the user suffers from blue-green colour vision deficiency.

Alternatively, optionally, the at least two other of the at least three different colours whose LEDs' brightness is selectively increased comprises a blue colour and a yellow colour, in case of the blue-yellow colour vision deficiency. This may be particularly applicable for a case where the at least three different colours comprise the red colour, the blue colour, the green colour and the yellow colour.

However, in another case, where the at least three different colours comprise the red colour, the blue colour and the green colour, the brightness of the LEDs of the blue colour with a shorter wavelength out of the at least two sets of LEDs of the blue colour having different spectral peaks and the brightness of the LEDs of the green colour with a longer wavelength out of the at least two sets of LEDs of the green colour having different spectral peaks may be increased.

The present disclosure also relates to the second aspect as described above. Various embodiments and variants disclosed above, with respect to the aforementioned first aspect, apply mutatis mutandis to the second aspect. The optional features of the first aspect apply to the second aspect.

Throughout the present disclosure, the "display apparatus" is a specialized equipment that is capable of at least displaying the images to the user via the liquid crystal display device. Optionally, the display apparatus is implemented as a head-mounted display (HMD). The term "head-mounted display" refers to a specialized equipment that is configured to present an XR environment to the user when said HMD, in operation, is worn by the user on his/her head. The HMD is implemented, for example, as an XR headset, a pair of XR glasses, and the like, that is operable to display a visual scene of the XR environment to the user. Optionally, in this regard, the given image is an XR image. The term "extended-reality" encompasses virtual reality (VR), augmented reality (AR), mixed reality (MR), and the like.

It will be appreciated that the processor is communicably coupled to the liquid crystal display device (and in particular, to the backlight unit) and at least one input means, wirelessly and/or in a wired manner. The processor is implemented as a hardware, a software, a firmware, or a combination of these. The processor is configured to control operation of the backlight unit, to receive the user input via the at least one input means, and also process the at least one control signal of the controller to display the images to the user via the liquid crystal display device.

The plurality of predefined options could be formulated based on at least one of: one or more colour vision deficiencies of the user, colour vision deficiencies experienced commonly by humans. The plurality of predefined options could be provided to the user in a form of at least one of: a clickable button, a menu, a checkbox, a slider, a toggle switch. The predefined extent to which the brightness of the LEDs of the at least one of the at least three different colours is to be selectively decreased can be selected as an extent at which the at least two other of the at least three colours are easily distinguishable. Such a predefined extent could differ for different users and for different types of colour vision deficiencies. The predefined extent may be provided in a form of at least one of: a percentage of total brightness of light emitted by the backlight unit via the array of LEDs, a lookup table, a ratio, a fuzzy logic. For example, when the user suffers from red-green colour vision deficiency, the given predefined option may correspond to selectively decreasing brightness of LEDs of the blue colour by 30 percent of a regular brightness level and of the white colour by 40 percent of the regular brightness level.

Optionally, the given predefined option also corresponds to at least two predefined extents to which brightness of LEDs of respective ones of the at least two other of the at least three different colours is to be selectively increased.

The at least one input means could be implemented as one of: a physical slider, a button, a remote control, a microphone, a haptic device. Hence, the user's selection could be in a form of any one of: a touch input, an audio input. The at least one input means provides a flexibility to the user using the display apparatus by allowing the user to conveniently choose the given predefined option, as and when required. This may, for example, be beneficial in a scenario where the user may require to see colours prominently only for a shorter duration of time during a typical day, such as when he/she wants to play a game. Furthermore, in this way, power resources of the display apparatus could also be saved.

The processor is at least communicably coupled to the controller of the backlight unit of the liquid crystal display device. Based on the one of the plurality of predefined options selected by the user, the processor is configured to send a signal to the controller in real time or in near-real time, which in turn selectively decreases the brightness of the LEDs of the at least one of the at least three different colours, as mentioned earlier.

The present disclosure also relates to the third aspect as described above. Various embodiments and variants disclosed above, with respect to the aforementioned first aspect, apply mutatis mutandis to the third aspect. The optional features of the first aspect apply to the second aspect.

Optionally, the at least three different colours comprise a red colour, a blue colour, a green colour, and a white colour. Alternatively, optionally, the at least three different colours comprise a red colour, a blue colour, and a green colour, wherein for two or more of the at least three different colours, LEDs of a given colour are divided into at least two sets of LEDs having different spectral peaks, respectively.

Optionally, the at least one of the at least three different colours whose LEDs' brightness is selectively decreased comprises at least one of: a blue colour, a white colour, a red colour.

Optionally, the at least one of the at least three different colours whose LEDs' brightness is selectively decreased comprises a white colour, wherein the step of driving the control circuit for selectively decreasing the brightness comprises driving the control circuit for selectively switching off the LEDs of the at least one of the at least three different colours in at least the part of said array.

Optionally, wherein the method further comprises driving the control circuit for selectively increasing a brightness of LEDs of at least two other of the at least three different colours in at least the part of said array. Optionally, the at least two other of the at least three different colours whose LEDs' brightness is selectively increased comprises any one of: (i) a red colour and a green colour, (ii) a blue colour and a green colour.

Optionally, the method further comprises:
receiving information indicative of a gaze direction of a user; and
selecting, based on the gaze direction of the user, the part of said array in which the brightness of the LEDs of the at least one of the at least three different colours is to be selectively decreased.

The present disclosure also relates to the fourth aspect as described above. Various embodiments and variants disclosed above, with respect to the aforementioned first aspect and the second aspect, apply mutatis mutandis to the fourth aspect. The optional features of the third aspect apply to the fourth aspect.

DETAILED DESCRIPTION OF THE DRAWINGS

Figure 2:
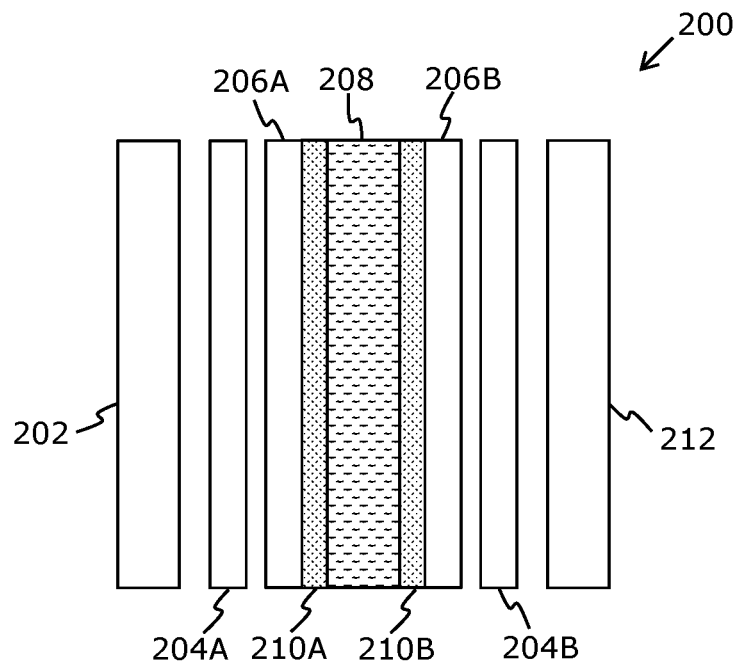
FIG. 2 illustrates an exploded view of a liquid crystal display device, in accordance with an embodiment of the present disclosure.

Referring to FIG. 2, illustrated is an exploded view of a liquid crystal display device 200, in accordance with an embodiment of the present disclosure. The liquid crystal display device 200 comprises a backlight unit 202, a first polarizer 204A, a second polarizer 204B, a first substrate 206A, a second substrate 206B, a liquid crystal material 208 encased between the first substrate 206A and the second substrate 206B, a first electrode 210A deposited on the first substrate 206A and disposed between the liquid crystal material 208 and the first substrate 206A, a second electrode 210B deposited on the second substrate 206B and disposed between the liquid crystal material 208 and the second substrate 206B, and a colour filter 212. Optionally, the first polarizer 204A is any one of a horizontal polarizer and a vertical polarizer, and the second polarizer 204B is another one of the vertical polarizer and the horizontal polarizer.

FIG. 2 is merely an example, which should not unduly limit the scope of the claims herein. A person skilled in the art will recognize many variations, alternatives, and modifications of embodiments of the present disclosure.

Figure 3:
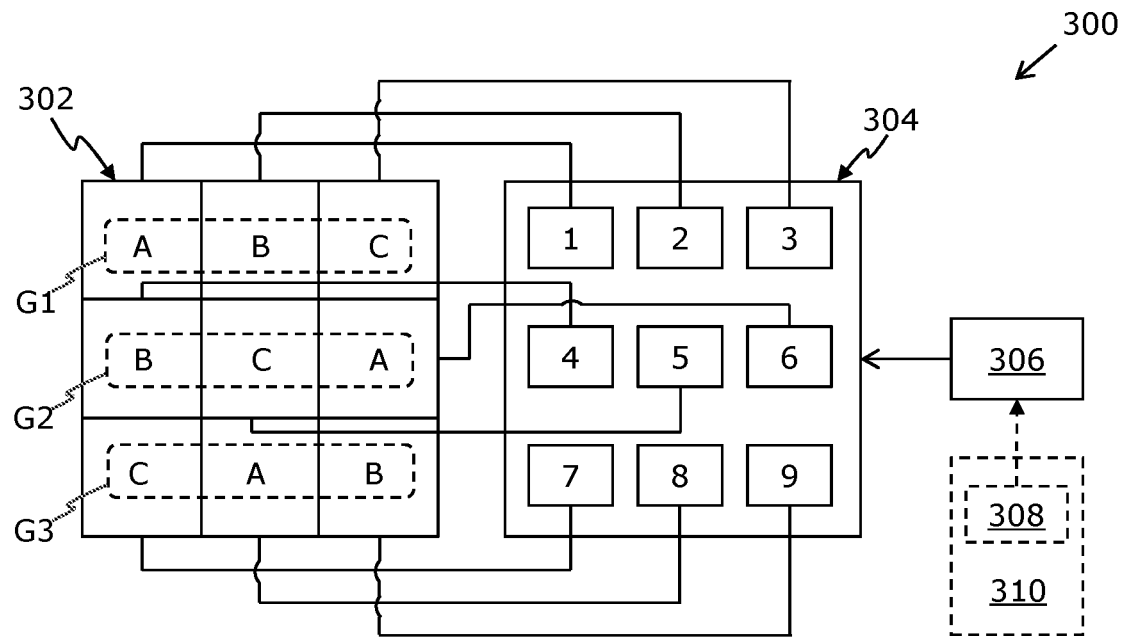
FIG. 3 illustrates a block diagram of an architecture of a backlight unit of a liquid crystal display device, in accordance with an embodiment of the present disclosure.

Referring to FIG. 3, illustrated is a block diagram of an architecture of a backlight unit 300 of a liquid crystal display device, in accordance with an embodiment of the present disclosure. The backlight unit 300 comprises an array 302 of light-emitting diodes (LEDs) of at least three different colours (depicted as LEDs A, B, and C of three different colours), a control circuit 304, and a controller 306. The LEDs A-C are arranged as groups G1, G2, and G3, of LEDs within said array 302, each group comprising at least one LED of each of the at least three different colours. The control circuit 304 is coupled with the array 302 of LEDs, wherein the control circuit 304 is to be employed to control individual LEDs of the at least three different colours in said array 302. The control circuit 304 is shown to optionally comprise sub-circuits 1-9 which are coupled with their corresponding LEDs in said array 302, to implement such individual controlling. The controller 306 is coupled to the control circuit 304 and said controller 306 is configured to drive the control circuit 304 to selectively decrease a brightness of the LEDs of at least one of the at least three different colours in at least a part of said array 302. Optionally, the controller 306 is communicably coupled to a gaze-tracking means 308. A display apparatus 310 optionally comprises the gaze-tracking means 308.

FIG. 3 is merely an example, which should not unduly limit the scope of the claims herein. A person skilled in the art will recognize many variations, alternatives, and modifications of embodiments of the present disclosure.

Figure 4A:
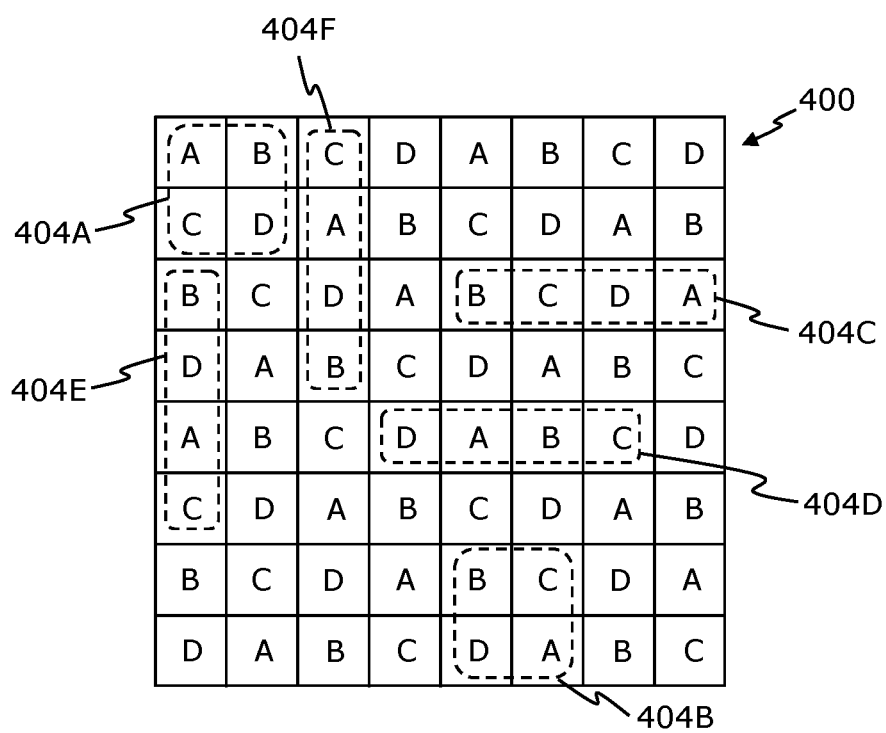
Figures 4B, 4C:
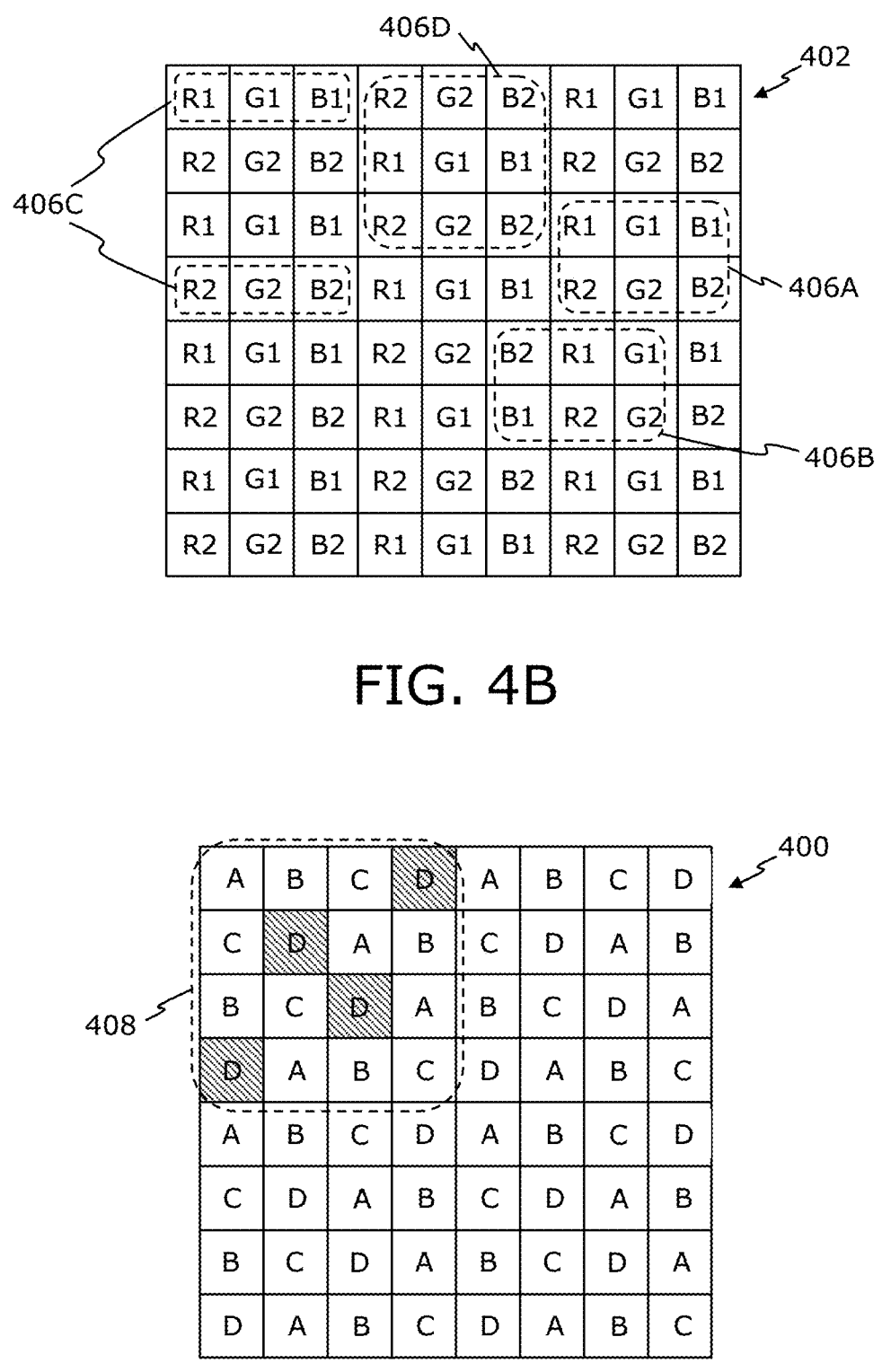

Referring to FIGS. 4A and 4B, illustrated are arrays (depicted as an array 400 in FIG. 4A and an array 402 in FIG. 4B) of light-emitting diodes (LEDs) of at least three different colours, in accordance with different embodiments of the present disclosure. In FIG. 4A, the array 400 of the LEDs is shown to comprise 64 LEDs that are arranged in a form of a two-dimensional matrix of 8×8 LEDS. The at least three different colours comprise a red colour, a blue colour, a green colour, and a white colour. The LEDs of the white colour are depicted as A, the LEDs of the blue colour are depicted as B, the LEDs of the green colour are depicted as C, and the LEDs of the red colour are depicted as D. The LEDS A-D of the array 400 are arranged as groups of LEDs within the array 400, each group shown to comprise one LED of each of the at least three different colours. These groups could comprise groups of LEDs arranged in a 2×2 matrix (such as groups 404A and 404B), or groups of LEDs arranged in a 1×4 matrix (such as groups 404C and 404D), or groups of LEDs arranged in a 4×1 matrix (such as groups 404E and 404F), or similar. Optionally, the array 400 of the LEDS A-D of the at least three different colours are arranged in such a manner that overall the white colour is produced uniformly, when all the LEDs A-D of the array 400 are switched on.

In FIG. 4B, the array 402 of the LEDs is shown to comprise 72 LEDs that are arranged in a form of a two-dimensional matrix 8×9 LEDs. The at least three different colours comprise a red colour, a blue colour, and a green colour. The LEDs of the red colour are divided into two sets of LEDs (depicted as LEDs R1 and R2) having different spectral peaks, the LEDs of the blue colour are divided into two sets of LEDs (depicted as LEDs B1 and B2) having different spectral peaks, the LEDs of the green colour are divided into two sets of LEDs (depicted as LEDs G1 and G2) having different spectral peaks. The LEDs R1, R2, B1, B2, G1, and G2 of the array 402 are arranged as groups of LEDs within the array 402, each group shown to comprise one LED of each of the at least three different colours. These groups could comprise groups of LEDs arranged in 2×3 matrices (such as a group 406A and 406B), or groups of LEDs arranged in two 1×3 matrices (such as groups 406C), or groups of LEDs arranged in a 3×3 matrix (such as a group 406D). Optionally, the array 402 of the LEDS R1, R2, B1, B2, G1, and G2 of at least three different colours are arranged in such a manner that overall the white colour is produced uniformly, when all the LEDs of the array 402 are switched on.

Referring to FIG. 4C, there is illustrated an exemplary part 408 of the array 400 of FIG. 4A in which a brightness of LEDs of at least one of the at least three different colours is to be selectively decreased, in accordance with an embodiment of the present disclosure. Optionally, a gaze direction of a user is used to select the part 408 of the array 400. For example, when the gaze direction of a user lies towards a top left portion of a liquid crystal display device in which the backlight unit is employed, a top left corner part of the array 400 is selected as the part 408. As an example, the user may suffer from red-green colour vision deficiency. Hence, in at least the part 408 of the array 400, a brightness of LEDs D of the white colour (depicted by a hatch pattern) is selectively decreased.

FIGS. 4A-4C are merely examples, which should not unduly limit the scope of the claims herein. A person skilled in the art will recognize many variations, alternatives, and modifications of embodiments of the present disclosure.

Figure 5A:
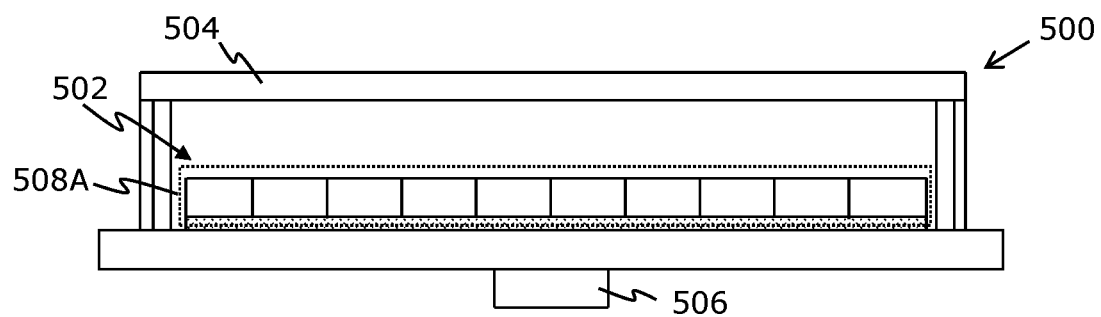
FIGS. 5A and 5B illustrate an arrangement of a backlight unit in a liquid crystal display device, in accordance with different embodiments of the present disclosure.
Figure 5B:
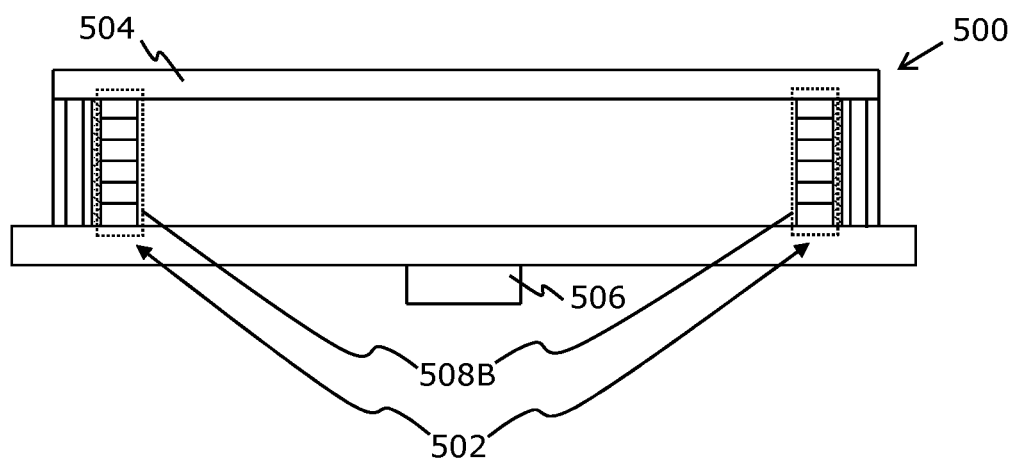

Referring to FIGS. 5A and 5B, illustrated is an arrangement of a backlight unit (depicted as a backlight unit 502) in a liquid crystal display device 500, in accordance with different embodiments of the present disclosure. In both FIGS. 5A and 5B, the liquid crystal display device 500 is shown to comprise a liquid crystal display unit 504 and a controller 506, apart from the backlight unit. A control circuit of the liquid crystal display device is not shown, for the sake of simplicity.

In FIG. 5A, the backlight unit 502 is shown to comprise an array 508A of light-emitting diodes (LEDs), wherein the controller 506 is coupled to the array 508A of LEDs via the control circuit. Herein, the array 508A of LEDs is arranged directly behind the liquid crystal display 504. Such a liquid crystal display device 500 is a bottom-lit liquid crystal display device. In FIG. 5B, the backlight unit 502 is shown to comprise an array 508B of LEDs, wherein the controller 506 is coupled to the array 508B of LEDs via the control circuit. Herein, the array 508B of LEDs is arranged around a perimeter edge behind the liquid crystal display unit 504. Such a liquid crystal display device 500 is an edge-lit liquid crystal display device.

FIGS. 5A and 5B are merely examples, which should not unduly limit the scope of the claims herein. A person skilled in the art will recognize many variations, alternatives, and modifications of embodiments of the present disclosure.

Figure 6:
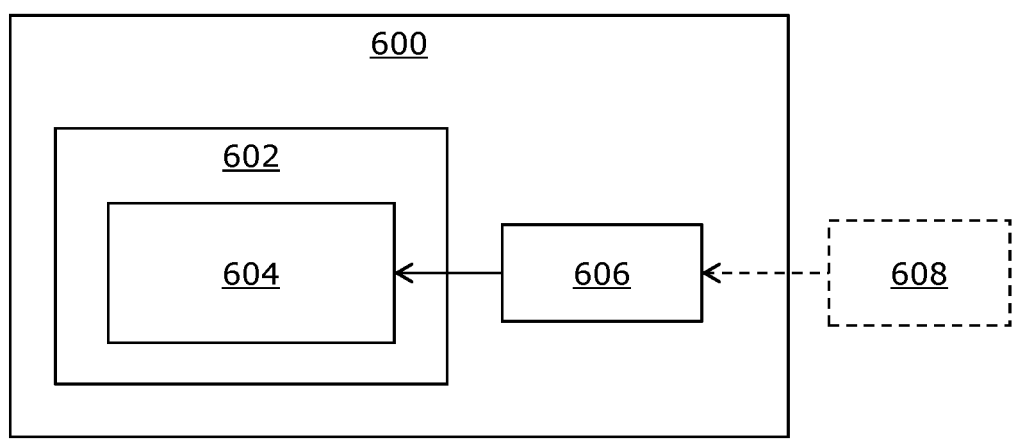
FIG. 6 illustrates a block diagram of a display apparatus, in accordance with an embodiment of the present disclosure.

Referring to FIG. 6, illustrated is a block diagram of a display apparatus 600, in accordance with an embodiment of the present disclosure. The display apparatus 600 comprises a liquid crystal display device 602 having a backlight unit 604 and a processor 606. The processor 606 is communicably coupled to the liquid crystal display device 602 (and in particular, to the backlight unit 604). The processor 606 is configured to perform various operations, as described earlier with respect to the aforementioned second aspect. Optionally, the display apparatus 600 further comprises at least one input means (as depicted by an input means 608), wherein the processor 606 is configured to receive a user input from the input means 608.

Figure 7:
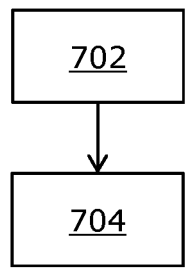
FIG. 7 illustrates steps of a method for illuminating, in accordance with an embodiment of a present disclosure.

FIG. 6 is merely an example, which should not unduly limit the scope of the claims herein. A person skilled in the art will recognize many variations, alternatives, and modifications of embodiments of the present disclosure.

Referring to FIG. 7, illustrated are steps of a method for illuminating, in accordance with an embodiment of a present disclosure. The steps of the method are implemented by a backlight unit of a liquid crystal display device, wherein the backlight unit comprises an array of light-emitting diodes (LEDs) of at least three different colours, wherein the LEDs are arranged as groups of LEDs within said array, each group comprising at least one LED of each of the at least three different colours, and a control circuit. At step 702, the control circuit is employed to control individual LEDs in said array. At step 704, the control circuit is driven for selectively decreasing a brightness of LEDs of at least one of the at least three different colours in at least a part of said array.

The aforementioned step are only illustrative and other alternatives can also be provided where one or more steps are added, one or more steps are removed, or one or more steps are provided in a different sequence without departing from the scope of the claims herein.

Figure 8:
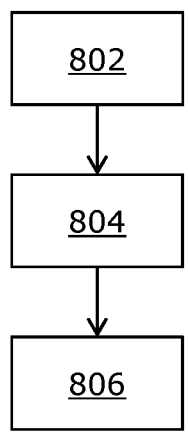
FIG. 8 illustrates steps of a method for displaying, in accordance with an embodiment of a present disclosure.

Referring to FIG. 8, illustrated are steps of a method for displaying, in accordance with another embodiment of a present disclosure. The steps of the method are implemented by a display apparatus comprising a liquid crystal display device having a backlight unit according to the first aspect of the present disclosure. At step 802, the backlight unit is driven, according to a plurality of predefined options, to display images to a user via the liquid crystal display device, wherein a given predefined option corresponds to a predefined extent to which the brightness of the LEDs of the at least one of the at least three different colours is to be selectively decreased. At step 804, a user input which is indicative of the user's selection of one of the plurality of predefined options, is received. At step 806, the backlight unit is driven according to the one of the plurality of predefined options selected by the user.

The aforementioned steps are only illustrative and other alternatives can also be provided where one or more steps are added, one or more steps are removed, or one or more steps are provided in a different sequence without departing from the scope of the claims herein.

What is claimed is:

1. A backlight unit of a liquid crystal display device, the backlight unit comprising:
    an array of light-emitting diodes (LEDs) of at least three different colours, wherein the LEDs are arranged as groups of LEDs within said array, each group comprising at least one LED of each of the at least three different colours;
    a control circuit that is to be employed to control individual LEDs in said array; and
    a controller configured to drive the control circuit to selectively decrease a brightness of LEDs of at least one of the at least three different colours in at least a part of said array;
    wherein the controller is further configured to:
        receive, from a gaze-tracking means, information indicative of a gaze direction of a user; and
        select, based on the gaze direction of the user, the part of said array in which the brightness of the LEDs of the at least one of the at least three different colours is to be selectively decreased.

2. The backlight unit of claim 1, wherein the at least three different colours comprise a red colour, a blue colour, a green colour, and a white colour.

3. The backlight unit of claim 1, wherein the at least three different colours comprise a red colour, a blue colour, and a green colour, wherein for two or more of the at least three different colours, LEDs of a given colour are divided into at least two sets of LEDs having different spectral peaks, respectively.

4. The backlight unit of claim 1, wherein the at least one of the at least three different colours whose LEDs' brightness is selectively decreased comprises at least one of: a blue colour, a white colour, a red colour.

5. The backlight unit of claim 1, wherein the at least one of the at least three different colours whose LEDs' brightness is selectively decreased comprises a white colour,
    wherein when selectively decreasing the brightness, the controller is configured to drive the control circuit to selectively switch off the LEDs of the at least one of the at least three different colours in at least the part of said array.

6. The backlight unit of claim 1, wherein the controller is further configured to drive the control circuit to selectively increase a brightness of LEDs of at least two other of the at least three different colours in at least the part of said array.

7. The backlight unit of claim 6, wherein the at least two other of the at least three different colours whose LEDs' brightness is selectively increased comprises any one of: (i) a red colour and a green colour, (ii) a blue colour and a green colour.

8. A display apparatus comprising:
    a liquid crystal display device having a backlight unit according to claim 1; and
    a processor configured to:
    drive the backlight unit, according to a plurality of predefined options, to display images to a user via the liquid crystal display device, wherein a given predefined option corresponds to a predefined extent to which the brightness of the LEDs of the at least one of the at least three different colours is to be selectively decreased;
    receive a user input indicative of the user's selection of one of the plurality of predefined options; and
    drive the backlight unit according to the one of the plurality of predefined options selected by the user.

9. A method for illuminating, the method being implemented by a backlight unit of a liquid crystal display device, wherein the backlight unit comprises an array of light-emitting diodes (LEDs) of at least three different colours, wherein the LEDs are arranged as groups of LEDs within said array, each group comprising at least one LED of each of the at least three different colours, and a control circuit, the method comprising:
    controlling, via the control circuit, individual LEDs in said array;
    driving the control circuit for selectively decreasing a brightness of LEDs of at least one of the at least three different colours in at least a part of said array;
    receiving information indicative of a gaze direction of a user; and
    selecting, based on the gaze direction of the user, the part of said array in which the brightness of the LEDs of the at least one of the at least three different colours is to be selectively decreased.

10. The method of claim 9, wherein the at least one of the at least three different colours whose LEDs' brightness is selectively decreased comprises at least one of: a blue colour, a white colour, a red colour.

11. The method of claim 9, wherein the at least one of the at least three different colours whose LEDs' brightness is selectively decreased comprises a white colour, wherein the step of driving the control circuit for selectively decreasing the brightness comprises driving the control circuit for selectively switching off the LEDs of the at least one of the at least three different colours in at least the part of said array.

12. The method of claim 9, wherein the method further comprises driving the control circuit for selectively increasing a brightness of LEDs of at least two other of the at least three different colours in at least the part of said array.

13. The method of claim 12, wherein the at least two other of the at least three different colours whose LEDs' brightness is selectively increased comprises any one of: (i) a red colour and a green colour, (ii) a blue colour and a green colour.

* * * * *